(12) United States Patent
Yokokawa et al.

(10) Patent No.: US 6,767,748 B2
(45) Date of Patent: Jul. 27, 2004

(54) SPOTTING PIN, SPOTTING DEVICE AND METHOD FOR SPOTTING BIOMOLECULES

(75) Inventors: Naoki Yokokawa, Tokyo (JP); Mitsuhiro Tachibana, Tokyo (JP); Hiroshi Kishida, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 10/429,825

(22) Filed: May 6, 2003

(65) Prior Publication Data

US 2003/0211013 A1 Nov. 13, 2003

(30) Foreign Application Priority Data

May 10, 2002 (JP) ........................................ 2002-136107

(51) Int. Cl.[7] ................................................. G01N 1/28
(52) U.S. Cl. .................... 436/180; 422/99; 422/100; 101/368; 347/110; 400/124.07; 400/124.29
(58) Field of Search .................... 422/99, 100; 436/180; 101/368; 347/110; 400/124.07, 124.29

(56) References Cited

U.S. PATENT DOCUMENTS

| 4,687,355 A | * | 8/1987 | Ikehata et al. | .......... 400/124.25 |
| 6,101,946 A | * | 8/2000 | Martinsky | .................... 101/494 |
| 2003/0035143 A1 | * | 2/2003 | Glemser et al. | ........... 358/1.16 |

FOREIGN PATENT DOCUMENTS

JP 2002-273944 A * 9/2002

* cited by examiner

Primary Examiner—Jan M. Ludlow
(74) Attorney, Agent, or Firm—Reed Smith LLP; Stanley P. Fisher, Esq.; Juan Carlos A. Marquez, Esq.

(57) ABSTRACT

The present invention enables the accurate management of the total number of spotting counts for each spotting pin. An IC chip is installed on the spotting pin to allow the IC chip to accumulate spotting-count information, and during each spotting time the information is loaded up and displayed.

8 Claims, 7 Drawing Sheets

Pin ID:  ABC123

Information history

| Year/month/day | Device in use | Position in Pin Head | Spotting times | Total of Spotting times |
|---|---|---|---|---|
| | | | | |
| | | | | |
| | | | | |
| | | | | |
| | | | | |

SPOTTING PIN, SPOTTING DEVICE AND METHOD FOR SPOTTING BIOMOLECULES

BACKGROUND OF THE INVENTION

1. Field of the Invention

The present invention relates to a spotting pin for spotting biomolecules such as DNAs on a spotting substrate and for preparing a biochip, a spotting device and a method for spotting.

2. Background Art

With respect to gene research and others, in biochemistry, microarrays or macroarrays (hereinafter referred to collectively as "biochip" in this specification) have conventionally been used for conducting experiments such as hybridization. The microarrays are prepared by spotting dense biomolecules such as DNAs or proteins for immobilization on substrates such as glass slides, nylons, or nitrocellulose membranes. The biochips are prepared by picking up a plurality of types of biomolecules dispensed in an MTP (Micro Titer Plate) by a plurality of spotting pins installed on a spotting device and spotting the same for immobilization on a substrate such as a glass slide or a membrane in accordance with predetermined arrays.

In order to assure the reliability of the results of experiments conducted using biochips, it is necessary that uniform amounts (quantities) of biomolecules are immobilized on each position on the biochip. Spotting pins installed on the spotting device are formed of a solid material such as stainless steel, and are prepared so that identical amounts of biomolecules are always spotted. However, when the number of spotting for immobilization reaches to approximately 100,000, the tips of the pins are gradually abraded away by the repeated contact with the substrate. When the spotting is carried out with a spotting pin with worn tip, spot shapes become varied, causing spot amounts to become unstable, and thereby giving rise to problems.

In order to continue to prepare high-quality biochips with the spotting device, it is necessary to accurately assess the conditions of the spotting pins installed on the device and to replace the spotting pins with new ones at appropriate times. If a spotting pin which has exceeded its service life continues to be used, the shape of the pin tip is changed by the contact friction, and consequently there is a high possibility of causing abnormal spot shapes. However, when the timing is premature, in that the spotting pin is replaced before its service life has expired, cost increases may be incurred.

Further, different types of biochips may be produced on a lot basis using the same spotting device. When an array pattern of spotting on a biochip for one lot is different from an array pattern for a subsequent lot, some of the plurality of spotting pins installed on the spotting device may be removed or additional spotting pins may be installed thereon. In such a case, since the plurality of the spotting pins installed on the spotting device do not have the same remaining days of service life, managing the timing of replaceing spotting pins becomes complicated.

Based on the recognition of such a problem regarding spotting devices or the spotting pins, an object of the present invention is to provide a spotting device which enables spotting pins to be replaced at appropriate times and can constantly produce high quality biochips, and a spotting pin therefor.

SUMMARY OF THE INVENTION

In order to accomplish the above object, the present inventors have developed a spotting system to automatically count the number of spottings of spotting pins and to record and manage them. In the spotting system according to the present invention, each spotting pin has an information recording medium such as an IC chip, and each independently accumulates spotting information. Further, an application program controls an IC chip reader/writer, installed on the spotting device, to perform reading/writing of the accumulated spotting information of each spotting pin.

Hereinafter, an embodiment of the present invention will be described.

According to the present invention, a spotting pin for spotting a biomolecule on a substrate comprises an information recording medium, wherein information concerning the total number of spotting counts is stored in the information recording medium.

A spotting device of the present invention comprises: a pin head having a spotting pin installed thereon, the spotting pin comprising an information recording medium that stores the total number of spotting counts; a pin head driving means for moving the pin head up and down; an information reading/writing means for reading and writing information on the information recording medium; a display section; and a control section for controlling the pin head driving means, information reading/writing means and display section, wherein the control section causes the display section to display the total number of spotting counts that the information reading/writing means reads out from the information recording medium provided on the spotting pin.

When the pin head has a plurality of spotting pins installed thereon, the display section displays the total number of spotting counts for each spotting pin. Further, the control section updates the total number of spotting counts displayed on the display section on a real time basis each time spotting is performed. Furthermore, the control section writes in the information recording medium provided on the spotting pin the updated total number of spotting counts of the spotting pin via the information reading/writing means. The total number of spotting counts for each spotting pin is displayed by a graphic such as a bar graph, and a display mode of the graphic such as color of the graphic is preferably modified in accordance with the total number of spotting counts.

A method for spotting a biomolecule according to the preset invention comprises the steps of: installing, on a pin head, a spotting pin comprising an information recording medium that stores the total number of spotting counts; reading the total number of spotting counts of the spotting pin from the information recording medium; displaying the read-out total number of spotting counts on a display means; spotting the biomolecule on a substrate using the spotting pin installed on the pin head; updating the total number of spotting counts displayed on the display means; and updating the total number of spotting counts stored in the information recording medium.

When the pin head has a plurality of spotting pins installed thereon, each spotting pin is identified based on spotting pin identification information recorded in the information recording medium provided on each spotting pin and the total number of spotting counts is displayed for each spotting on the display means.

In the present invention, an IC chip may be used as the information recording medium. Further, as the information reading/writing means, an IC chip reader/writer may be used.

The term "biomolecule" used herein means a biopolymer such as DNAs, RNAs and proteins, which are immobilized on glass slides, nylon membranes or the like and used as probes to cause hybridization with target biomolecules in a sample.

The spotting system of the present invention is suitable for mass production of high quality biochips.

This specification includes part or all of the contents as disclosed in the specification and/or drawings of Japanese Patent Application No. 2002-136107, which is a priority document of the present application.

DESCRIPTION OF THE INVENTION

Hereinafter, one example for accomplishing the present invention will be described in detail by referring to the accompanying drawings.

A DNA spotting device for spotting DNAs as biomolecules will be described hereinafter. Moreover, inarguably the present invention can also be applied to the spotting of biomolecules other than DNAs.

Figure 1:
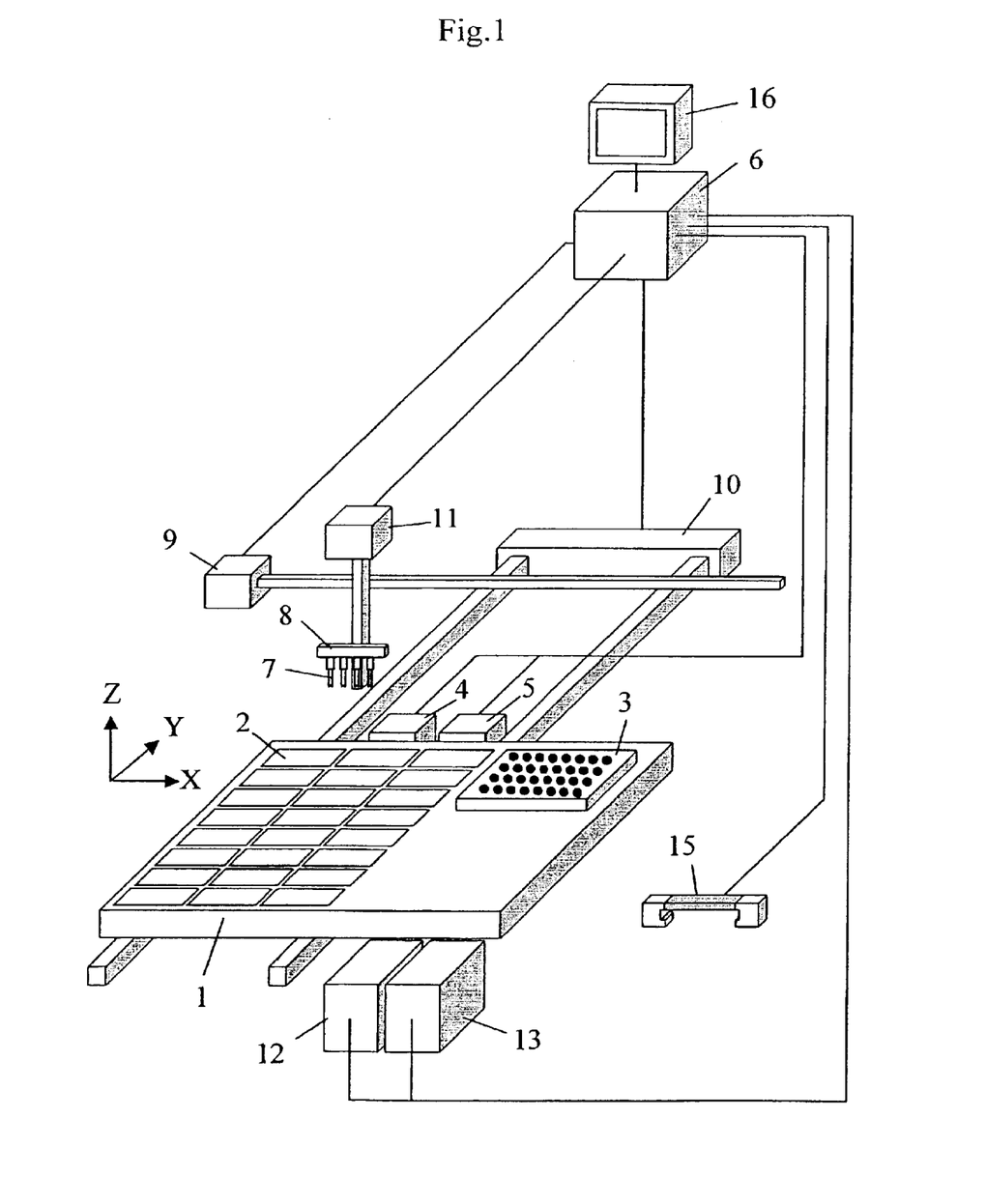
FIG. 1 is a schematic view showing one example of a DNA spotting device according to the present invention.

FIG. 1 is a schematic view showing one example of a DNA spotting device of the present invention. This DNA spotting device is provided with a tray 1 having glass slides 2 (membranes) and a micro titer plate 3 (MTP) placed thereon, a pin head 8 having a plurality of spotting pins 7 installed thereon, a pin washing tank 4, a pin drying tank 5, a washing tank 12, a drain tank 13, an X-axis driving motor 9, a Y-axis driving motor 10, a Z-axis driving motor 11, an IC chip reader/writer 15, and a control section 6. The control section 6 is connected to a display section 16. The pin head 8 having spotting pins 7 installed thereon moves along the direction of the X-axis and the Z-axis with the X-axis driving motor 9 and Z-axis driving motor 11. The tray 1 having the glass slides 2 (membranes) and the MTP 3 placed thereon moves along the direction of the Y-axis with the Y-axis driving motor 10.

Figure 2:
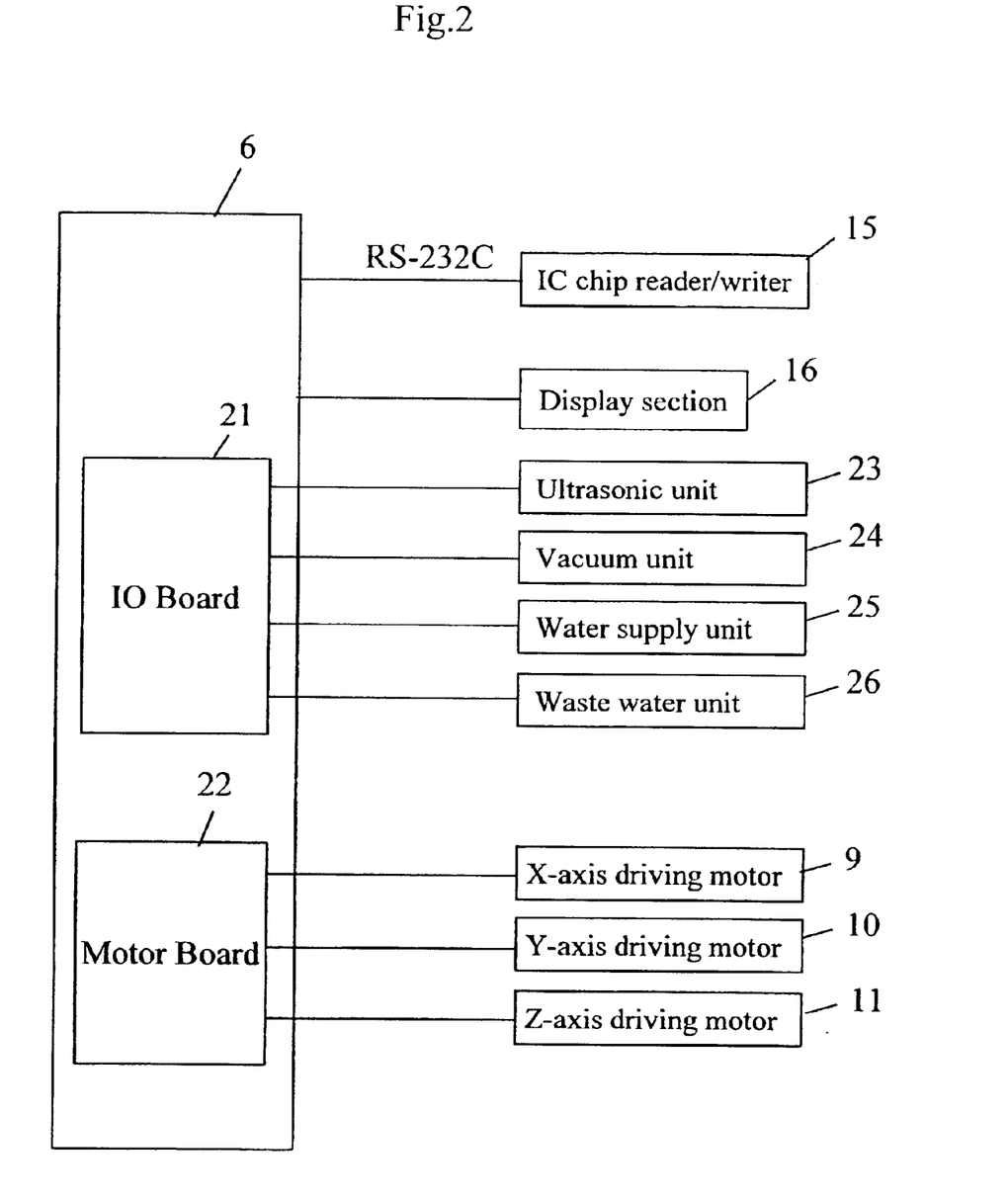
FIG. 2 is a functional block diagram of the spotting device shown in FIG. 1.

FIG. 2 is a functional block diagram of the spotting device as shown in FIG. 1. The IC chip reader/writer 15 is connected to the control section 6 through an RS232C, and controlled with an application program. The control section 6 has an IO Board 21 and a motor board 22. The IO Board 21 controls an ultrasonic unit 23 for the pin washing tank 4, a vacuum unit 24 for the drying tank 5, a water supply unit 25, and a waste water unit 26. The motor board 22 controls motors 9, 10, and 11 for the respective axes. Further, the control section 6 controls the display conditions of the display section 16.

Figure 3A:
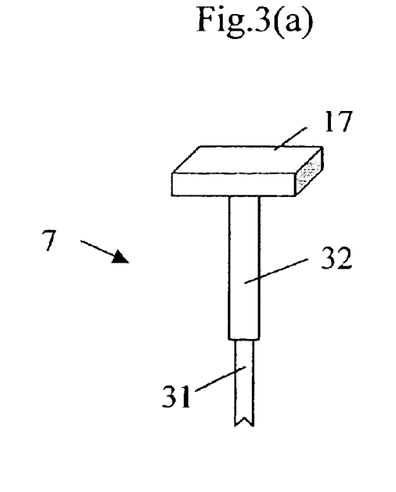
FIGS. 3(a) and 3(b) are schematic views showing a structure example of a spotting pin.
Figure 3B:
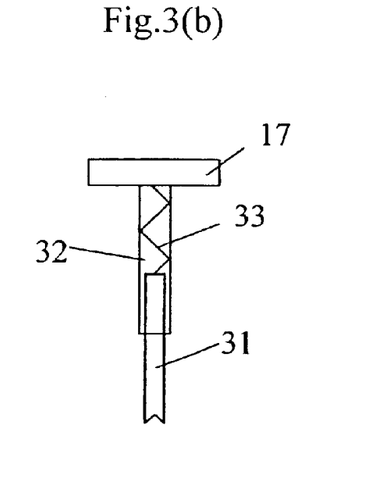

FIGS. 3(a) and 3(b) are schematic views showing an example structure of the spotting pin. FIGS. 3(a) and 3(b) are a perspective view and a sectional side view, respectively. The spotting pin 7 shown in the figures has a stick-like pin main body 31 with a recess formed on its tip and a sheath portion 32 having the pin main body inserted thereinto. The sheath portion 32 has a spring 33 placed therein so that the spring pushes the other tip of the pin main body 31. In this way, by placing the spring inside the spotting pin, the pressure applied to the pin tip during spotting time is reduced. Further, the spotting pins of the present invention each have an IC chip 17 installed thereon. The IC chip stores a pin ID for each spotting pin which has had the IC chip attached thereto and the spotting information that has been accumulated so far therein. Although the spotting pin shown in the figures has the IC chip installed on a tail portion thereof, the IC chip may be installed on any position.

Figure 4:
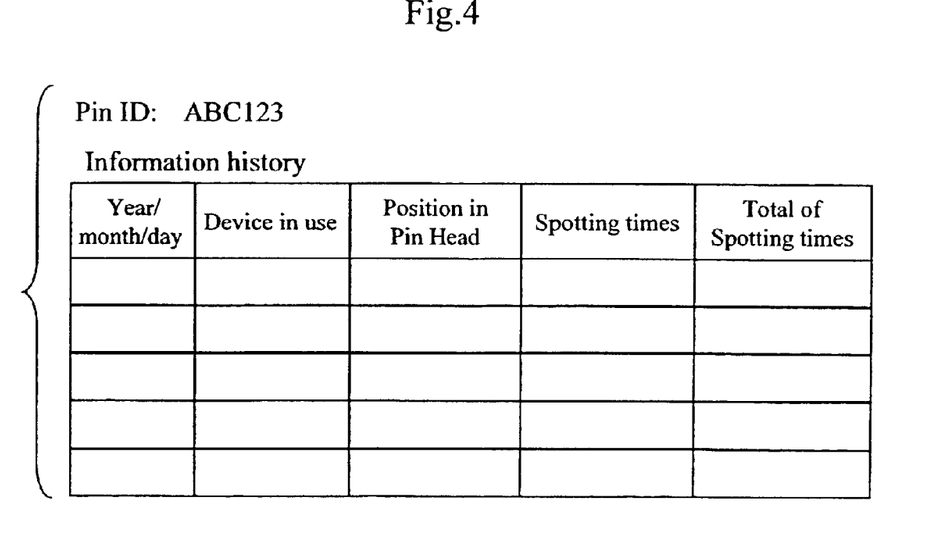
FIG. 4 is a view showing an example of data stored on an IC chip.

FIG. 4 is a view showing an example of data stored on the IC chip installed on the spotting pin. In the IC chip 17, information history on spotting as well as an identification mark (number) for identifying individual spotting pins are recorded. The information history on spotting includes a date when each spotting was carried out, identification information on a spotting device used therefor, information indicating the installation position of the spotting pin of the pin head, the number of spotting conducted by the device, and the total number of spotting counts that have been made so far.

Figure 5A:
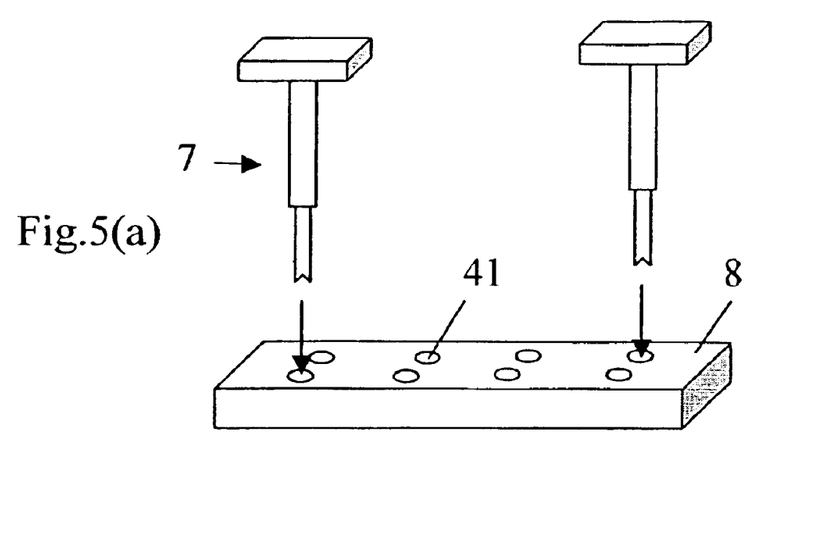
FIGS. 5(a) and 5(b) are schematic views of a pin head.
Figure 5B:
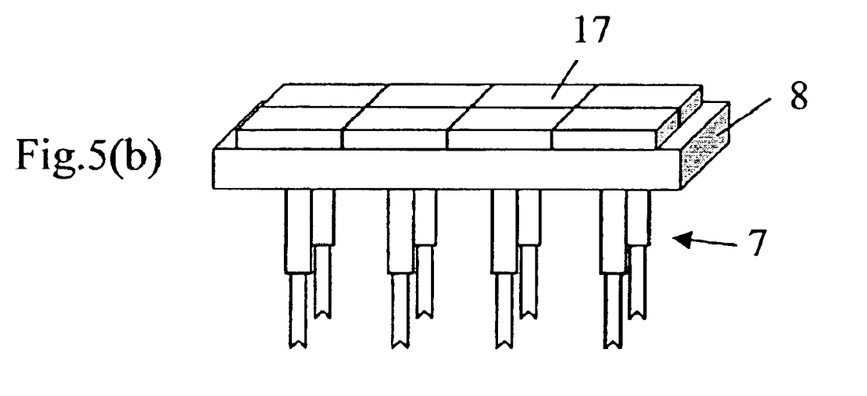

FIGS. 5(a) and 5(b) are schematic views of the pin head. FIG. 5(a) is a schematic view showing a method for installing spotting pins 7 on the pin head 8. FIG. 5(b) is a schematic and perspective view of the pin head having spotting pins installed thereon. The pin head 8 of the present embodiment has eight pin installation holes 41 in total, which are for installing spotting pins and is arranged in two rows. The sheath 32 of each spotting pin is fixed into the pin head by inserting from above into the pin installation hole 41. On the upper portion of the pin head 8, IC chips 17 of the installed spotting pins 7 are arranged. FIG. 5(b) shows the condition wherein spotting pings are installed on all the installation holes, but there are some cases wherein spotting is conducted while some installation holes do not have spotting pins, in other words using only three holes among the four installation holes on a single row.

Figure 6:
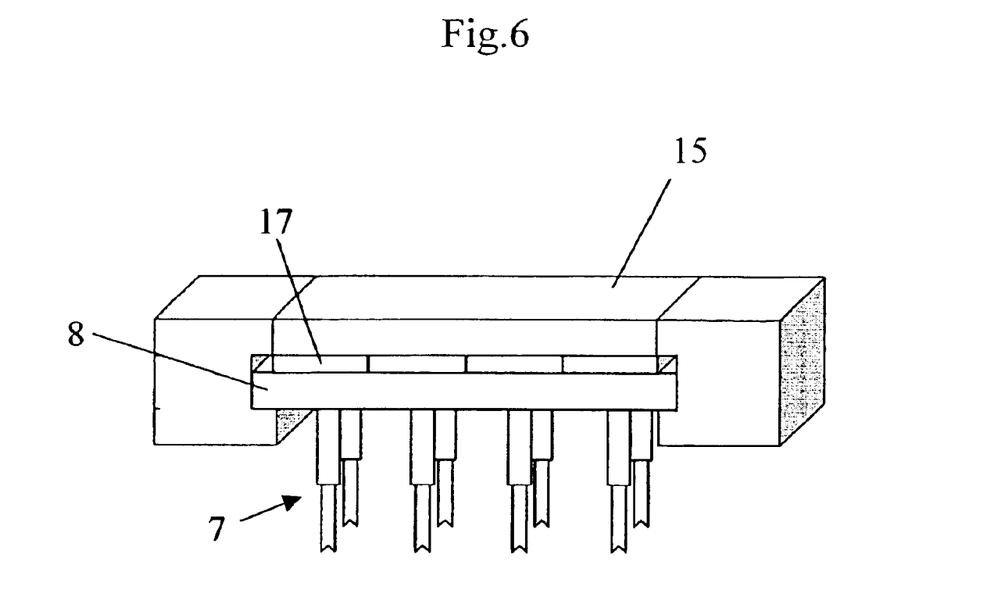
FIG. 6 is a view showing reading/writing of information of the IC chip by an IC chip reader/writer.

The IC chip reader/writer 15 installed on the spotting device can read and write information of the IC chip 17 possessed by the spotting pin. FIG. 6 is a view showing the condition wherein the pin head having spotting pins installed thereon is passed through the IC chip reader/writer so that the IC chip reader/writer reads information of individual IC chips or writes information. The IC chip 17 is preferably a type of IC chip, from and to which the IC chip reader/writer 15 can read and write information without the need for contact.

A sequence of spotting operations by the spotting device as shown in FIG. 1 comprises: moving the pin head 8 to the washing tank 4 and washing the spotting pins 7; moving the pin head 8 to the drying tank 5 and drying the spotting pins; picking up DNA samples from the MTP 3; and spotting the samples on the glass slide 2 (membrane). The above operations are repeatedly conducted with different DNA samples and different glass slides 2 (membranes). Deionized water in the washing tank 4 is supplied from the wash tank 12, and the waste liquid after washing is collected into a drain tank 13. Ultrasonic waves and vacuum are used for washing and drying, respectively, and they are each controlled by the application program that the control section 6 has loaded up.

The number and arrangement of spotting pins installed on the pin head can be selected within a certain range, and information regarding the arrangement of spotting pins on the pin head is inputted into the application program. The application program n controls spotting based on a spotting method optimum for each type of pin arrangement.

Figure 7:
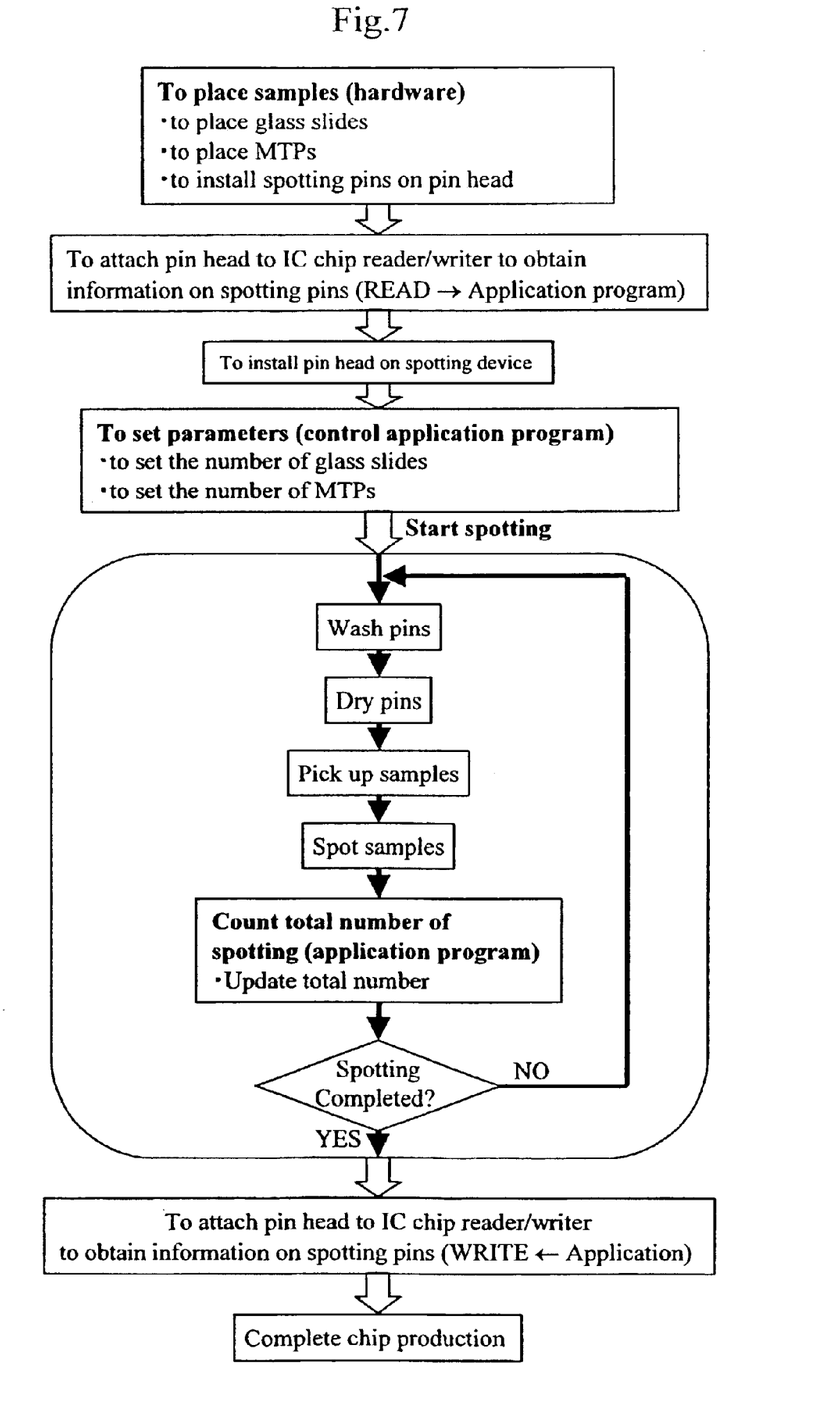
FIG. 7 is a view explaining spotting processes according to the present invention.

FIG. 7 is a view explaining spotting processes according to the present invention. First, a certain number of glass slides to be prepared and an MTP having DNA samples dispensed therein are placed on the main body of a spotting device. Further, spotting pins 7 with IC chips are installed on the pin head 8. Next, as shown in FIG. 6, the pin head 8 with spotting pins installed thereon is passed through an IC chip reader/writer 15 so that a control section 6 loads up accumulated spotting information of each spotting pin into the application program. Thereafter, accumulated spotting data for each spotting pin is displayed on an application program screen of the spotting device.

Figure 8:
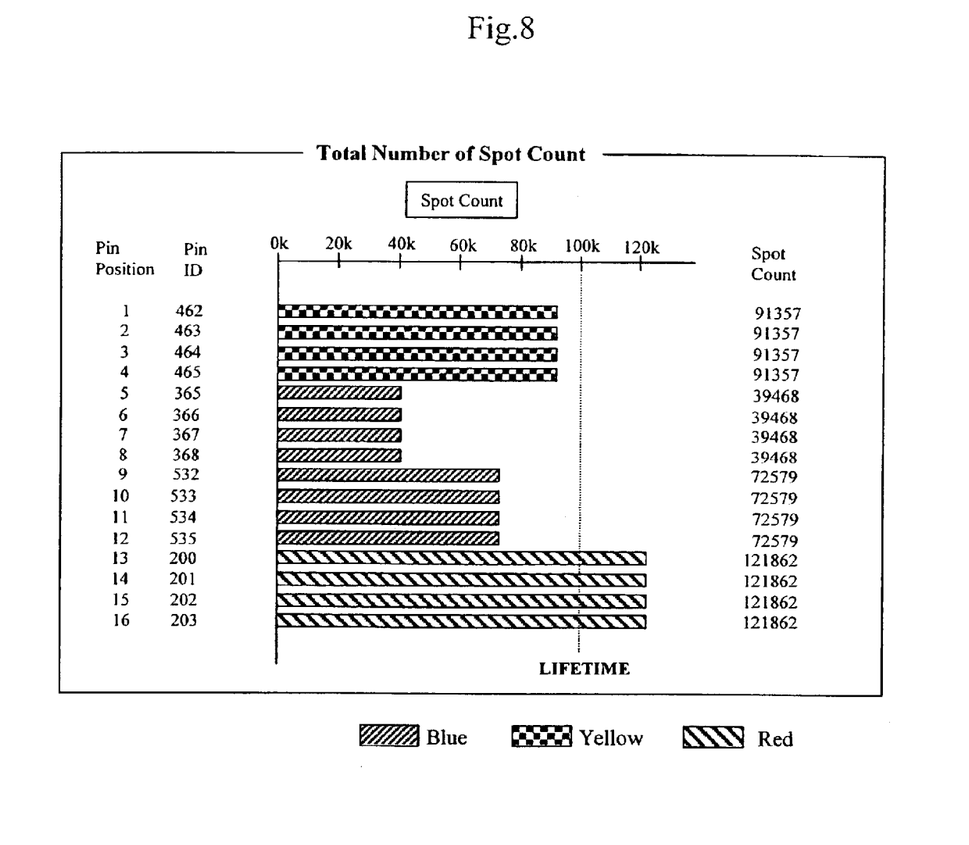
FIG. 8 is a view showing a display example of an application program screen.

FIG. 8 shows an example display (an application program screen) of the display section. On the screen of the display section 16, an ID of a pin installed on the pin head and the total number of spotting counts that have been carried out so far are displayed for each pin position number on the pin head. The example of the figure shows a case of a pin head that has 16 pin installation positions. Also, the figure shows an example wherein the spotting pin is controlled by regarding the total number of spotting counts of 100,000 as the service life of each spotting pin, in other words using it as an index of timing for pin replacement.

The total number of spotting counts for each pin is represented by a numerical value, and is also represented by a graphic such as a bar graph so that the relationship between approximate number of usage times and service life can be grasped at a glance. In the bar graph, a bar for a pin that has sufficient remaining time of service life is colored in blue. When a pin has the total number of spotting counts close to 100,000 and almost reaches to the end of the service life, a bar for such a pin is colored in yellow to draw operators' attention. When a pin has a total number of spotting counts that exceeds 100,000 or is reaching near the end of its service life, a bar for such a pin is colored in red to indicate warning. In the way shown above, a display mode is varied depending on total number of spotting counts.

In the example display of the figure, spotting pins installed on the pin head are classified into four groups, based on the total number of spotting counts of the spotting pin, which reflects usage status thereof. A group of pin IDs 365 to 368 and a group of pin IDs 532 to 535 are represented by blue, so that they have sufficient time until the end of the service life. A group of pin IDs 200 to 203, which have been used most frequently, is represented by red. This means that they have been used over the service life of 100,000 times. Other group of pin IDs 462 to 465 comes closer to the end of their service life. These matters can be grasped at a glance. In addition, accurate figures on the total number of spotting counts are displayed simultaneously. Thus, when an operator looks at them, the operator can easily ascertain the status of individual spotting pins and determine the timing of their replacements. In the case shown in the figure, the operator gets to judge if four spotting pins installed in Pin Position 13 to 16 should be used as they are or should be replaced with other spotting pins.

Next, the pin head 8 is installed on the spotting device, and a spotting condition is inputted through the application program. At this time, the number of glass slides, the number of MTPs and the like are inputted. Thereafter, spotting is initiated. First, the pin head 8 is moved to the washing tank 4 for washing the tips of the pins. The washed pin tips are dried in the drying tank 5. Next, DNA samples are picked up from the MTP 3 and spotted on the glass slide 2 (membrane). At this moment, the total number of spotting counts is updated by one on the application program, and the updated figure is displayed on the screen on a real time basis. This process is repeated for the number of times designated by preset conditions until the spotting is completed.

After the spotting is completed, the pin head is removed from the spotting device and installed again on the IC chip reader/writer 15. Then, the total number of spotting counts on the application program is written on the IC chip 17 of each spotting pin 7 to update data on the IC chip. At this time information other than the number of spotting counts, for example, the date when spotting was conducted, identification information of the spotting device, and installation position on the pin head, may simultaneously be loaded up.

Although the above example shows that the IC chip reader/writer is independent from the main body of the spotting device, the IC chip reader/writer may, for example, be configured so that it is integrated with a pin head installation member of the spotting device, or fixed at a position of the device close to the pin head position. This allows an operator to omit the operation of passing the pin head having spotting pins installed thereon through the IC chip reader/writer, and thus only the installation of the pin head on the spotting device enables the reading of information recorded on the IC chip or the writing of information on the IC chip. Therefore, after completing the spotting, errors for updating spotting-count information can be avoided, which are caused by forgetting to pass the pin head through the IC chip reader/writer.

As described above, according to the present invention, the total number of spotting counts for each spotting pin can be accurately managed, and thus it is easy to tell the end of service life for each pin and determine a suitable timing for pin replacement based on the total number of spotting counts for each pin, thereby enabling a stable supply of high quality biochips without misjudging the timing for pin replacement.

All publications, patents and patent applications cited herein are incorporated herein by reference in their entirety.

What is claimed is:

1. A spotting pin for spotting a biomolecule on a substrate, comprising an electronic information recording medium, wherein the electronic information recording medium stores information regarding the total number of spotting counts.

2. A spotting device for spotting a biomolecule on a substrate comprising:
   a pin head having a spotting pin installed thereon, the spotting pin comprising an electronic information recording medium that stores the total number of spotting counts;
   a pin head driving means for moving the pin head up and down;
   an electronic information reading/writing means for reading and writing information on the electronic information recording medium;
   a display section; and
   a control section for controlling the pin head driving means, the electronic information reading/writing means, and the display section,
   wherein the control section causes the display section to display the total number of spotting counts that the electronic information reading/writing means reads out from the electronic information recording medium provided on the spotting pin.

3. The spotting device according to claim 2, wherein the display section displays the total number of spotting counts for each spotting pin.

4. The spotting device according to claim 2, wherein the control section updates on a real time basis the total number of spotting counts displayed on the display section during spotting.

5. The spotting device according to claim 2, wherein the control section writes the updated total number of spotting counts of the spotting pin in the electronic information recording medium provided on the spotting pin via the electronic information reading/writing means.

6. The spotting device according to claim 2, wherein the total number of spotting counts for each spotting pin is displayed on the display section by a graphic and a display mode of the graphic is modified in accordance with the total number of spotting counts.

7. A method for spotting a biomolecule comprising the steps of:

installing, on a pin head, a spotting pin comprising an electronic information recording medium that stores the total number of spotting counts;

reading the total number of spotting counts of the spotting pin from the electronic information recording medium;

displaying on a display means the loaded-up total number of spotting counts;

spotting the biomolecule on the substrate using the spotting pin installed on the pin head;

updating the total number of spotting counts displayed on the display means; and updating the total number of spotting counts stored in the electronic information recording medium.

8. The method according to claim 7, wherein a plurality of spotting pins installed on the pin head are identified based on spotting pin identification information recorded in the electronic information recording medium and the total number of spotting counts for each spotting are displayed on the display means.

* * * * *